United States Patent
Hoogenboom et al.

(10) Patent No.: US 12,037,456 B2
(45) Date of Patent: Jul. 16, 2024

(54) POLY(2-OXAZOLINE)S AND METHODS FOR PREPARING THEM

(71) Applicant: Universiteit Gent, Ghent (BE)

(72) Inventors: Richard Hoogenboom, Terneuzen (NL); Ondrej Sedlacek, Velke Prilepy (CZ)

(73) Assignee: Universiteit Gent, Ghent (BE)

( * ) Notice: Subject to any disclaimer, the term of this patent is extended or adjusted under 35 U.S.C. 154(b) by 573 days.

(21) Appl. No.: 17/293,669

(22) PCT Filed: Nov. 14, 2019

(86) PCT No.: PCT/EP2019/081309
§ 371 (c)(1),
(2) Date: May 13, 2021

(87) PCT Pub. No.: WO2020/099553
PCT Pub. Date: May 22, 2020

(65) Prior Publication Data
US 2022/0010068 A1     Jan. 13, 2022

(30) Foreign Application Priority Data

Nov. 14, 2018 (EP) .................................... 18206173

(51) Int. Cl.
| | |
|---|---|
| *C08G 73/02* | (2006.01) |
| *A61K 9/16* | (2006.01) |
| *A61K 47/34* | (2017.01) |
| *A61K 47/59* | (2017.01) |
| *A61L 29/08* | (2006.01) |
| *C08G 85/00* | (2006.01) |

(52) U.S. Cl.
CPC ........ *C08G 73/0233* (2013.01); *A61K 9/1641* (2013.01); *A61K 47/34* (2013.01); *A61K 47/59* (2017.08); *A61L 29/085* (2013.01); *C08G 85/002* (2013.01); *A61L 2400/10* (2013.01); *A61L 2400/18* (2013.01); *C08G 2150/00* (2013.01)

(58) Field of Classification Search
CPC .............. C08G 73/0233; C08G 85/002; C08G 2150/00; A61K 47/59; A61K 9/1641; A61K 47/34; A61L 29/085; A61L 2400/10; A61L 2400/18
See application file for complete search history.

(56) References Cited

U.S. PATENT DOCUMENTS

2014/0011964 A1*    1/2014   Harris .................. A61K 38/193
                                                     525/417

FOREIGN PATENT DOCUMENTS

WO      2016008817 A1     1/2016

OTHER PUBLICATIONS

International Search Report mailed Feb. 17, 2020 in eference to co-pending European PCT/EP2019/081309 filed Nov. 14, 2019.
(Continued)

*Primary Examiner* — Shane Fang
(74) *Attorney, Agent, or Firm* — Dinsmore & Shohl LLP

(57) ABSTRACT

The present invention, in general, relates to the field of poly(2-oxazolines) (PAOx), more in particular poly(2-methoxymethyl-2-oxazoline) (PMeOMeOX) and poly(2-dimethylamino-2-oxazoline) (PDMAOx). The present invention also provides methods for preparing these PAOx, as well as compositions and uses comprising said PAOx.

11 Claims, 6 Drawing Sheets

(56) References Cited

OTHER PUBLICATIONS

European Search Report in reference to co-pending European Application No. EP18206173 filed Nov. 24, 2019.
Written Opinion mailed Feb. 17, 2020 in co-reference to pending European PCT/EP2019/081309 filed Nov. 14, 2019.
Bloksma, et al., "Thermoresponsive Poly(2-oxazine)s" Marcomolecular Rapid Communications, Macromolecular Journals, vol. 33, pp. 92-96, 2012.
Callahan, et al., "Semitelechelic HPMA Copolymers Functionalized with Triphenylphosphonium as Drug Carriers for Membrane Transduction and Mitochondrial Localization" Biomacromolecules, pp. 2347-2356, Aug. 2006.
Das, et al., "Activated Ester Containing Polymers: Opportunities and Challenges for the Design of Functional Macromolecules", Chemical reviews, vol. 116, pp. 1434-1495, 2016.
Kagiya et al., "Ring-opening Polymerization of 2-Substituted 2-Oxazolines", Polymer Letter, vol. 4, pp. 441-445, 1966.
Mees, et al., "Full and partial hydrolysis of poly(2-oxazoline)s and the subsequent post-polymerization modification of the resulting polyethylenimine (co)polymers", Polymer Chemistry, vol. 9, pp. 4968-4978, 2018.
Mees, et al., Functional Poly(2-oxazoline)s by Direct Amidation of Methyl Ester Side Chains, Macrmolecules, vol. 48, pp. 3531-3538, 2015.
Mees, et al., "Sweet Polymers: Poly(2-ethyl-2-oxazoline) Glycopolymers by Reproductive Amination", Bio Macromolecules, vol. 17, pp. 4027-4036, 2016.
Verbraeken, et al., "The Chemistry of poly(2-oxazoline)s", European Polymer Journal, vol. 88, pp. 451-469, 2017.

* cited by examiner

POLY(2-OXAZOLINE)S AND METHODS FOR PREPARING THEM

CROSS REFERENCES TO RELATED APPLICATIONS

This application is a national-stage application under 35 U.S.C. § 371 of International Application No. PCT/EP2019/081309, filed Nov. 14, 2019, which International Applications claims the benefit of priority to European Patent Application No. 18206173.9, filed Nov. 14, 2018.

FIELD OF THE INVENTION

The present invention, in general, relates to the field of poly(2-oxazolines) (PAOx), more in particular poly(2-methoxymethyl-2-oxazoline) (PMeOMeOX) and poly(2-dimethylamino-2-oxazoline) (PDMAOx). The present invention also provides methods for preparing these PAOx, as well as compositions and uses comprising said PAOx.

BACKGROUND TO THE INVENTION

The synthesis of well-defined biopolymers continues to attract substantial attention in chemical and biomedical research, playing the key role in the construction of systems for drug/gene delivery or tissue engineering. In the last decade, poly(2-alkyl-2-oxazoline)s (PAOx) gained considerable popularity due to their synthetic versatility and tunable properties. The polymer properties can be modulated by selecting appropriate side-chain substituents, chain-end functional groups and the polymer chain length.

Within this class, poly(2-ethyl-2-oxazoline) (PEtOx) and poly (2-methyl-2-oxazoline) (PMeOx) have found widespread biomedical applications resulting from their hydrophilicity, biocompatibility, non-immunogenicity and flexibility. These properties are often superior to those of the other polymers extensively used in biomedical research (e.g., polyethylene oxide or poly(N-(2-hydroxypropyl) methacrylamide)).

Well-defined PAOx can be synthesized by living cationic ring-opening polymerization (CROP) of their respective monomers with alkyl tosylates being the most common initiators (Verbraeken et al., 2017). The polymerization is terminated by nucleophiles providing an easy route for introduction of chain-end functionality by simply selecting the appropriate terminating agent. Under strictly inert conditions, the CROP of 2-oxazolines proceeds without termination and chain transfer side reactions, yielding polymers with narrow molar mass distribution. The polymerization time can be substantially reduced by employing pressurized high temperature conditions, e.g. using microwave irradiation, yielding polymers within a couple of minutes. Finally, the potential of PAOx was further enhanced by the recent discovery of a synthetic procedure for the preparation of defined high molar mass PAOx (WO2016008817A1).

Despite the synthetic versatility and broad applicability, the synthesis of PAOx still presents some major challenges. As the propagating oxazolinium chain-ends react with nucleophiles, monomers bearing such groups (e.g., free amines, alcohols, thiols, carboxylic acids) cannot be polymerized by CROP. This can be solved by employing suitable protective groups, followed by the post-polymerization deprotection. Furthermore, CROP cannot be utilized for monomers that interfere with standard polymerization process (e.g., monomers bearing aliphatic bromide or tosylate) or monomers rapidly degrading at elevated temperature. As the preparation of new, highly functionalized PAOx is desirable, the search for alternative synthetic strategies provides an appealing quest in polymer chemistry.

The living character of CROP allows us to synthesize a wide range of copolymer architectures including statistical, gradient or block copolymers. Recently, Mees et al reported an alternative route to PAOx copolymers consisting in the partial acidic hydrolysis of PEtOx homopolymer to statistical PEtOx-PEI copolymers, that were further modified by acylation using methyl succinyl chloride (Mees et al., 2015). This post-polymerization strategy might be the only effective way to synthesize statistical copolymers, where different reactivities of respective monomers lead to copolymers with strong gradient of composition (e.g., 2-phenyl-2-oxazoline with MeOx). In another study, the PEtOx-PEI copolymer was exploited in the synthesis of glycopolymers using reductive amination reaction (Mees et al., 2016).

Despite many reports on full hydrolysis of PAOx to well-defined PEI, the reverse reaction, i.e., the complete acylation (at least 95% conversion) of PEI yielding defined PAOx homopolymers was not yet employed for the preparation of novel PAOx. In fact, most previous reports focused on partial acylation of L-PEI to prepare functional L-PEI (Mees et al., 2018). Nonetheless, the complete reacylation of PEI obtained from hydrolysis of poly(2-methyl-2-oxazoline) with acetic anhydride was only shown in one of the first papers reporting the CROP of 2-oxazolines (Kagiya et al.; 1966). This reacetylation method of PEI towards PAOx synthesis might be an elegant alternative to the conventional cationic ring-opening polymerization, especially in the case of unstable monomers or functional monomers interfering with the polymerization process.

Herein, we describe such a protocol for the straightforward synthesis of defined functional PAOx, via acylation of PEI, that are not straightforward synthesizable via the monomer. To demonstrate its versatility, a series of new hydrophilic PAOx was prepared and their physical, chemical and biological properties were studied by different techniques with emphasis on their potential in biomedical research. More specifically, a series of PAOx having defined oligoether side chains is reported, which was inspired by the high hydrophilicity and good antifouling behavior of the structurally related methoxyethyl-substituted polypeptoid. Furthermore, our attempts to prepare the 2-methoxyethyl-2-oxazoline monomer revealed that it is unstable and undergoes spontaneous elimination of methanol, partially, yielding 2-vinyl-2-oxazoline, indicating the need for an alternative pathway to prepare such PAOx with this oligoether side chains.

Herein, we describe a new method for the synthesis of superhydrophilic poly(2-alkyl-2-oxazoline)s (PAOx) from poly(2-ethyl-2-oxazoline) (PEtOx). A well-defined linear polyethyleneimine was prepared from PEtOx by full acidic hydrolysis of its side-chains followed by re-acylation with different carboxylic acids. Using this protocol, we obtained a series of new hydrophilic PAOx containing side-chain ether groups with potential in the biomaterials science. The relative hydrophilicity of polymers was assessed, revealing that poly(2-methoxymethyl-2-oxazoline) (PMeOMeOx) is the most hydrophilic PAOx to date. Additionally, the amorphous poly(2-methoxy-ethoxy-ethoxymethyl-2-oxazoline) (PDEGOx) shows the lowest reported glass transition temperature (−25° C.) within the PAOx family to date. The biomedical potential of prepared polymers was further fortified by an in vitro cytotoxicity study, where all polymers appeared to be non-cytotoxic. The described synthetic protocol is universal and can be extremely versatile, especially for PAOx that are difficult to prepare by conventional cationic ring opening polymerization due to the monomer interference and/or degradation.

SUMMARY OF THE INVENTION

In a first aspect, the present invention provides a polyoxazoline selected from the list comprising: poly(2-methoxymethyl-2-oxazoline) (PMeOMeOx) and poly(2-dimethylamino-2-oxazoline) (PDMAOx).

In a particular embodiment, the present invention provides a copolymer comprising at least one polyoxazoline of the present invention.

The current invention further provides a composition comprising at least one polyoxazoline as defined herein and/or at least one copolymer as defined herein; in combination with one or more active ingredients, preferably one or more active pharmaceutical ingredients, even more preferably one or more hydrophilic active pharmaceutical ingredients.

In a further embodiment, the present invention provides a substrate having attached thereto, or associated therewith, one or more polyoxazolines as defined herein and/or one or more copolymer as defined herein.

In a particular embodiment, the substrate of the present invention may be selected from the list comprising: polymeric supports, metal and metal oxide supports, glass and quartz supports and silicium supports. Said substrate may for example be selected from the list comprising: (bio)medical implants, drug delivery carriers, biosensors, and marine coatings.

The present invention also provides a polyoxazoline or a copolymer as defined herein for use in human or veterinary medicine.

In a further aspect, the present invention provides the use of a substrate as defined herein, in anti-biofouling, blood half-life extension, or lubrication.

The present invention also provides the use of a polyoxazoline or a copolymer as defined herein, in surface modification of a substrate.

In a further aspect, the present invention provides a method for the preparation of superhydrophilic poly(2-oxazoline)s; said method comprising the steps of:
a) preparing a linear polyethyleneimine (PEI) from "starting polyoxazolines" by controlled acidic hydrolysis of its side-chains with at least 95% hydrolysis; and
b) re-acylation of the side-chains of the product obtained from step a) using carboxylic acid or carboxylic acid chloride or other activated esters, to reacylate at least 95% of the secondary amine groups.

In a specific embodiment, the present invention provides a method as defined herein, for the preparation of a polyoxazoline as defined herein; wherein said "starting polyoxazolines" are poly(2-ethyl-2-oxazoline) (PEtOx), poly(2-methyl-2-oxazoline) (PMeOx), poly(2-n-propyl-2-oxazoline) (PnPrOx) or poly(2-isopropyl-2-oxazoline) (PiPrOx). Wherein said carboxylic acid is methoxyacetic acid in the preparation of poly(2-methoxymethyl-2-oxazoline) (PMeOMeOx); wherein said carboxylic acid chloride is or N,N-dimethylcarbamoyl chloride in the preparation of poly(2-dimethylamino-2-oxazoline) (PDMAOx).

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
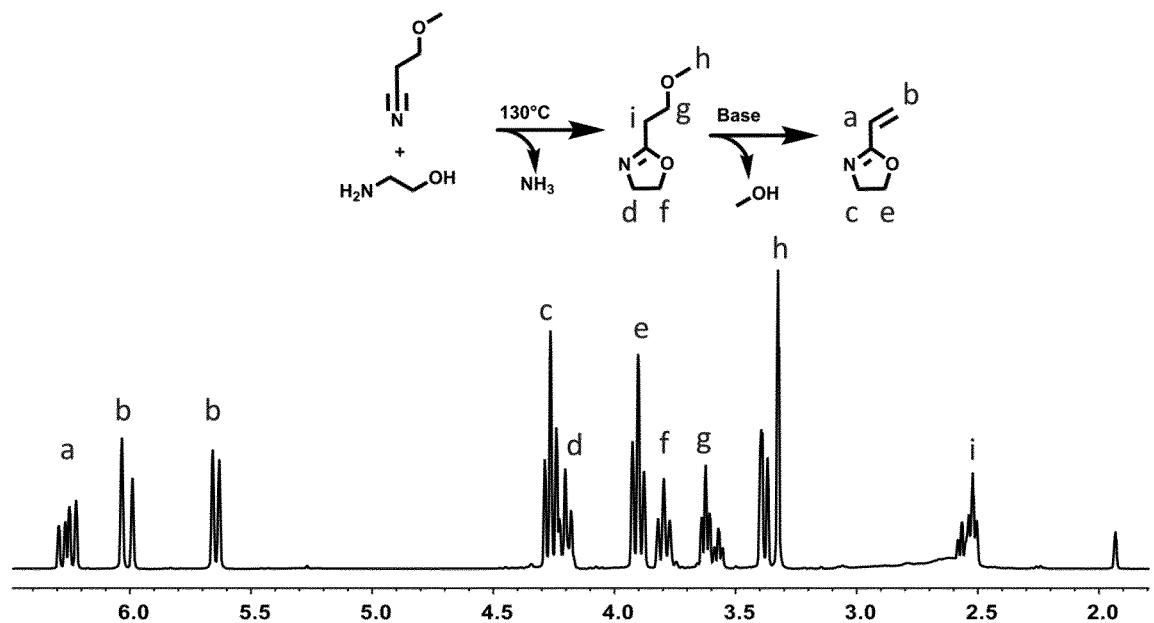
FIG. 1. The synthesis of 2-methoxyethyl-2-oxazoline (MeOEtOx) using the Witte-Seelinger method and the in-situ E1cB-elimination under basic condition (imine and/or ammonia) towards 2-vinyl-2-oxazoline (VinOx) resulting in a mixture of both. The ratio of the MeOEtOx/VinOx mixture was 1:2 (bottom—$^1$H NMR spectra). During the destillation of this crude mixture no pure 2-oxazoline could be isolated.

As already detailed herein above, in a first aspect, the present invention provides a polyoxazoline selected from the list comprising: poly(2-methoxymethyl-2-oxazoline) (PMeOMeOx) and poly(2-dimethylamino-2-oxazoline) (PDMAOx).

In the context of the present invention, PMeOMeOx is generally represented as follows:

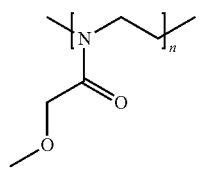

wherein n can be any integer from 10 to 2000, in particular n is from about 10 to about 500; more in particular from about 50 to about 200; even more in particular n is about 80 in one specific example.

In the context of the present invention, PDMAOx is generally represented as follows:

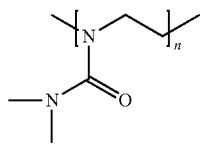

wherein n can be any integer from 10 to 2000, in particular n is from about 10 to about 500; more in particular from about 50 to about 200; even more in particular n is about 80 in one specific example.

The poly(2-oxazoline)s as used in the present invention preferably have a number average molar mass as between 5,000 g/mol and 200,000 g/mol; preferably between 10,000 g/mol and 100,000 g/mol.

In a particular embodiment, the present invention provides a copolymer comprising at least one polyoxazoline of the present invention. Hence, the copolymer of the present invention comprises at least one of poly(2-methoxymethyl-2-oxazoline) (PMeOMeOx) and poly(2-dimethylamino-2-oxazoline) (PDMAOx); or a combination thereof.

The current invention further provides a composition comprising at least one polyoxazoline as defined herein and/or at least one copolymer as defined herein; optionally in combination with one or more active ingredients, preferably one or more active pharmaceutical ingredients, even more preferably one or more hydrophilic active pharmaceutical ingredients.

In another embodiment of the invention, the polymer compositions according to the invention may also comprise other excipients in addition to the poly(2-oxazoline)s. These other excipients can be polymer excipients selected from the list including, but not limited to, hydroxyproplylmethylcellulose, xanthan gum, methacrylic acid copolymers, ethylcellulose, or polyvinylpyrrolidon. Furthermore, the polyoxazolines of the present invention can be combined with pharmaceutical excipients to produce pharmaceutical dosage forms, such as one or more fillers, pigments, colorants, flavourings, binders, plasticizers, antioxidants, lubricants, permeability enhancers, solid diluents and/or liquid diluents.

However, the presence of these other excipients is not essential for the polymer combination or composition according to the present invention. Hence, in a specific embodiment, the present invention provides a polymer composition as claimed herein which does not comprise further excipients or components other than the enclosed polymers and (where applicable) active ingredients.

Active ingredients according to the invention can include pharmaceutical ingredients, nutrients, cosmeceuticals, diagnostic agents, and nutritional agents.

The active ingredients that may be administered using the formulations, systems and methods of the invention are not limited, as the invention enables the effective delivery of a wide variety of active ingredients, in particular hydrophilic active ingredients.

The term active pharmaceutical agent as used herein refers to therapeutic, diagnostic, or prophylactic pharmaceutical and veterinary agents as well as other agents. In an another embodiment, the active pharmaceutical ingredient and also the pharmaceutical composition according to the different embodiments of the invention is for use as a human or veterinary medicine.

The one or more active pharmaceutical ingredients can be selected from any of the various classes of such ingredients including, but not limiting to, analgesic agents, anesthetic agents, anti-anginal agents, anti-arthritic agents, anti-arrhytmic agents, anti-asthmatic agents, antibacterial agents, anti-BPH agents, anticancer agents, anticholinergic agents, anticoagulants, anticonvulsants, antidepressants, antidiabetic agents, antidiarrheals, anti-epileptic agents, antifungal agents, antigout agents, antihelminthic agents, antihistamines, antihyperstensive agents, anti-inflammatory agents, antimalarial agents, antimigraine agents, antimuscarinic agents, antinauseants, antineoplastic agents, anti-obesity agents, anti-osteoporosis agents, antiparkinsonism agents, antiprotozola agents, antipruritics, antipsychotic agents, antipyretics, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics e.g. hydrochlorothiazide (HCT), gastro-intestinal agents, genetic material, histamine receptor antagonists, homonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotene, nutritional oils, parasympatholytic agents, sedatices, sex hormones, sympathomimetic agents, tranquilizers, vasodilators, vitamins, and combinations thereof.

In a specific embodiment, the active pharmaceutical ingredients of the present invention are hydrophilic (i.e. soluble in water and other polar substances), for example selected from metoprolol tartrate (MPT), metformin hydrochloride (MTF), and theophylline anhydrous (Theo). The present invention is also directed to a polymer combination according to one or more of the previous embodiments wherein said polymer combination is selected from the list comprising a (polyoxazoline) polymer blend or a polyoxazoline copolymer. A blend as used herein is considered as a polymer mixture in which two or more polymers are blended. In a preferred embodiment, all components of the blend are in powder form.

The polyoxazines or (co-)polymers thereof of the present invention are useful in making biofilm-resistant coatings (i.e., coatings that resist biofilm formation and/or enhance the release of formed biofilms, as evidenced by resistance to the growth of at least one microorganism). Thus, methods of coating a substrate to improve biofilm resistance of the substrate (relative to the uncoated substrate) are provided by the present disclosure. In one embodiment, a coating composition is provided that includes a polyoxazine of the present disclosure and a solvent, whereby the coating compositions are applied to substrates to impart a biofilm-resistant coating thereto.

The substrate on which the coating can be disposed for the formation of a biofilm-resistant coating can be any of a wide variety of materials. Useful substrates include ceramics, siliceous substrates including glass, metal, natural and man-made stone, woven and nonwoven articles, polymeric materials, including thermoplastics and thermosets, including, for example, poly(meth)acrylates, polycarbonates, polystyrenes, styrene copolymers such as styrene acrylonitrile copolymers, polyesters, polyethylene terephtalate, silicones such as that used in medical tubing, paints such as those based on acrylic resins, powder coatings such as polyurethane or hybrid powder coatings, and wood. The substrate can be in the form of a film, woven, or nonwoven, for example. In a very specific embodiment, the substrate is selected from the list comprising: polymeric supports, metal and metal oxide supports, glass and quartz supports and silicium supports; alternatively said substrate may also be selected from the list comprising: (bio)medical implants, drug delivery carriers, biosensors, and marine coatings.

Various articles can be effectively treated with the coating composition of the present invention to provide a biofilm-resistant coating thereon. The present invention also provides a coated article, such as a film. Thus, the present disclosure provides an article comprising a substrate (e.g., a film), wherein the substrate includes at least one surface having a layer that includes a (co)polymer of the present disclosure disposed thereon.

Preferably, the substrate to which coating is to be applied should be clean prior to application to obtain optimum characteristic and durability. Metallic as well as glass surfaces are often covered with organic contaminants. Before the coatings of the invention can be applied to such surfaces, they should be cleaned by at least solvent wiping. In the case of gross contamination, the metallic or glass surface may have to be etched, anodized, or treated in ways known to those skilled in the art. For example, if the surface of steel is coated with rust, that rust may have to be etched away by an acid treatment. Once the surface of the metal is exposed, the coating can be applied.

Biofilms typically develop where the substrate is in contact with water or exposed to humid conditions. The coatings of the present disclosure retard the formation of such biofilms, particularly when exposed to circulating water. It is believed that the microorganisms are unable or minimally able to attach to the coated surfaces. Further, it is believed that extant biofilms are more easily removed from the coated surface. Thus, the compositions of the present invention are particularly suited for substrate in wet or humid environments such as in medical catheter coatings, antifouling marine coatings, coatings for water handling equipment, heat exchangers and other HVAC equipment, coatings for filter media, and dental equipment, devices and materials that may be used in the oral cavity.

The present invention thus also provides the use of a substrate as defined herein in human or veterinary medicine. More in particular, the present invention provides the use of a substrate as defined herein in anti-biofouling, blood half-life extension, or lubrication.

In a further aspect, the present invention provides the use of one or more polyoxazolines of the present invention in surface modification of a substrate.

In a further embodiment, the present invention provides a substrate having attached thereto, or associated therewith, one or more polyoxazolines as defined herein and/or one or more copolymer as defined herein.

In a further aspect, the present invention provides a method for the preparation of superhydrophilic poly(2-oxazoline)s; said method comprising the steps of:
  a) preparing a linear polyethyleneimine (PEI) from "starting polyoxazolines" by controlled acidic hydrolysis of its side-chains; and
  b) re-acylation of the side-chains of the product obtained from step a) using carboxylic acid or carboxylic acid chloride.

In a specific embodiment, of the method of the present invention, the hydrolysis degree and re-acylation degree is at least 95%. Hence, the present invention also provides a method for the preparation of superhydrophilic poly(2-oxazoline)s; said method comprising the steps of:
  a) preparing a linear polyethyleneimine (PEI) from "starting polyoxazolines" by controlled acidic hydrolysis of its side-chains with at least 95% hydrolysis; and
  b) re-acylation of the side-chains of the product obtained from step a) using carboxylic acid, carboxylic acid chloride or activated esters, to reacylate at least 95% of the secondary amine groups.

In the context of the present invention, the term "hydrolysis degree" is meant to be the fraction (or percentage) of the total side-chains which are hydrolysed. The aim of the method is to obtain full hydrolysis, i.e. at least 95-100% of the side-chains are hydrolysed; corresponding to a degree of hydrolysis of about 0.95 to 1.00. In the context of the present invention, the term "re-acylation degree" is meant to be the fraction (or percentage) of the total side-chains which are re-acylated. The aim of the method is to obtain full re-acylation, i.e. at least 95-100% of the side-chains are re-acylated; corresponding to a degree of re-acylation of about 0.95 to 1.00. The term activated esters is used to describe carboxylic acid groups having a good leaving group making them reactive towards amines. Examples of such activated esters include but are not limited to N-hydroxysuccinimide esters, sulfo-N-hydroxysuccinimide esters, pentafluorophenyl esters and siacylic acid esters (Das et al., 2016).

Superhydrophilicity refers to the phenomenon of excess hydrophilicity, or attraction to water; in superhydrophilic materials, the contact angle of water is equal to zero degrees. Practically, it is used herein to describe polymers that are more hydrophilic than poly(2-methyl-2-oxazoline). In the present invention it was unexpectedly found that combining the poly(2-oxazoline) backbone with short oligoether or dimethylamino side-chains leads to materials that are more hydrophilic than anticipated based on the individual components.

In a further aspect, the present invention provides a method for the preparation of poly(2-oxazoline)s; said method comprising the steps of:
  a) preparing a linear polyethyleneimine (PEI) from "starting polyoxazolines" by controlled acidic hydrolysis of its side-chains (at least 95%); and
  b) re-acylation of the side-chains (at least 95%) of the product obtained from step a) using carboxylic acid or carboxylic acid chloride;
  wherein said carboxylic acid is not acetic anhydride.

In a particular embodiment of the method of the present invention, step a) comprises:
  a1) dissolving "starting polyoxazoline" in hydrochloric acid and incubating it overnight under argon atmosphere;
  a2) removing all volatiles and suspending the crude PEI hydrochloride as obtained from step a1) in water;
  a3) adding sodium hydroxide to the suspension of step a3) until said crude PEI hydrochloride first dissolves and subsequently precipitates as a free base of PEI at a pH of about 10-11;
  a4) filtering, washing and recrystallizing said PEI as obtained from step a3) to obtain a linear PEI as defined herein.

In a particular embodiment of the method of the present invention, step b) comprises:
  b1) dissolving carboxylic acid chloride or a mixture carboxylic acid with an amidation coupling reagent in polar organic solvent
  b2) adding tertiary amine base to the mixture obtained from step b1)

b3) transferring the mixture obtained from step b2) into a solution of linear PEI as obtained from step a), in polar organic solvent b4) incubating said mixture obtained from b3) overnight under argon atmosphere b5) evaporating the solvent from the mixture obtained from step b4), thereby obtaining said superhydrophilic poly(2-oxazoline).

In a specific embodiment, the present invention provides a method as defined herein, for the preparation of a polyoxazoline as defined herein; wherein one or more of the following applies:

said "starting polyoxazolines" may be poly(2-ethyl-2-oxazoline) (PEtOx), poly(2-methyl-2-oxazoline) (PMeOx), poly(2-n-propyl-2-oxazoline) (PnPrOx) or poly(2-isopropyl-2-oxazoline) (PiPrOx);

said carboxylic acid may be methoxyacetic acid in the preparation of poly(2-methoxymethyl-2-oxazoline) (PMeOMeOx);

said carboxylic acid chloride may be N,N-dimethylcarbamoyl chloride in the preparation of poly(2-dimethylamino-2-oxazoline) (PDMAOx);

said amidation coupling reagent may be selected from the list comprising benzotriazol-1-yl-oxytripyrrolidinophosphonium hexafluorophosphate (PyBOP), benzotriazol-1-yloxytris(dimethylamino)phosphonium hexafluorophosphate (BOP), (7-azabenzotriazol-1-yloxy)tripyrrolidinophosphonium hexafluorophosphate (PyAOP), 1-[bis(dimethylamino)methylene]-1H-1,2,3-triazolo[4,5-b]pyridinium 3-oxid hexafluorophosphate (HATU), 2-(1H-benzotriazol-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), 1,1'-carbonyldiimidazole (CDI), 1,1'-thiocarbonyldiimidazole (TCDI), (3-(diethoxyphosphoryloxy)-1,2,3-benzotriazin-4(3H)-one) (DEPBT), 4-(4,6-dimethoxy-1,3,5-triazin-2-yl)-4-methyl-morpholinium chloride (DMTM), N,N'-dicyclohexylcarbodiimide (DCC), N,N'-diisopropylcarbodiimide (DIC) or 1-ethyl-3-(3-dimethylaminopropyl)carbodiimide (EDC);

said polar organic solvent may be selected from the list comprising N, N-dimethyl formamide (DMF), N,N-dimethyl acetamide (DMA), N-methylpyrrolidone (NMP), dimethyl sulfoxide (DMSO) or sulfolane.

Finally, the present invention provides polyoxazolines obtainable using the methods of the present invention.

Examples

Materials.

2-Ethyl-2-oxazoline (EtOx) was kindly donated by Polymer Chemistry Innovation and was distilled over $CaH_2$ before use. Methyl p-toluenesulfonate (MeOTs) was obtained from Sigma-Aldrich and was distilled from $CaH_2$ prior to use. (Benzotriazol-1-yloxy)tripyrrolidinophosphonium hexafluorophosphate (PyBOP) was purchased from Sigma-Aldrich and was used as received. Acetonitrile (Sigma-Aldrich) was purified over aluminum oxide using a solvent purification system from J. C. Meyer. All other chemicals, including acetic acid, 2-ethanolamine, 3-methoxypropionitrile, methoxyacetic acid, ethoxyacetic acid, 3-methoxypropionic acid, 3-ethoxypropionic acid, [2-(2-methoxyethoxy)ethoxy]acetic acid, N,N-diisopropylethylamine (DIPEA), fluorescein-5-isothiocyanate (FITC) and DL-dithiothreitol (DTT) were purchased from TCI Europe and were used as received.

Synthesis of 2-methoxyethyl-2-oxazoline (MeOEtOx)

A suspension of $Zn(OAc)_2.2H_2O$ (10.97 g, 0.05 mol, 0.05 equiv.) in 2-ethanolamine (80.7 g, 1.32 mol, 1.2 equiv.) and 3-methoxypropionitrile (93.7 g, 100 ml, 1.10 mol, 1 equiv.) was heated to 130° C. for 14 hours until no 3-methoxypropionitrile was detected anymore by gas chromatography (GC). The obtained product consisted of a 1:2 mixture of MeOEtOx and 2-vinyl-2-oxazoline (VinOx) resulting from elimination of methanol as determined by $^1$H-NMR spectroscopy (FIG. 1). Attempts to purify the MeOEtOx by distillation led to further elimination of methanol. Therefore, this route was not further pursued.

Synthesis of poly(2-ethyl-2-oxazoline) (PEtOx)

In the glove-box, the monomer EtOx (10 g, 101 mmol) and the initiator MeOTs (152 µL, 1.0 mmol, [EtOx]: [MeOTs]=100:1) were dissolved in dry acetonitrile (15.2 mL) and stirred at 80° C. for 3 h. Then, a sample for GC was taken and the mixture was cooled down to room temperature, followed by termination with solid $NaN_3$ (328 mg, 5.1 mmol) overnight. The GC analysis revealed 79% conversion of the monomer. The reaction mixture was precipitated in cold diethyl ether, filtered and dried under reduced pressure. The crude polymer was dissolved and purified by dialysis (MWCO=1 kDa) against distilled water followed by freeze-drying to obtain PEtOx (7.3 g, 73%) as a white powder.

Synthesis of Poly(Ethylene Imine) (PEI)

PEtOx (8 g) was dissolved in aqueous hydrochloric acid (~18 wt. %, 80 mL) and refluxed overnight (14 h) under argon atmosphere. All volatiles were then removed under vacuum and the crude PEI hydrochloride was suspended in ice-cold distilled water (80 mL). Ice-cold aqueous sodium hydroxide (2 M) was added dropwise to the suspension until it dissolved, but with further addition of NaOH, the free base of PEI precipitated at pH 10-11. The precipitate was filtered, washed with distilled water, recrystallized twice from the same solvent and dried under high vacuum to obtain PEI as a white powder (3.1 g, 88%). $M_n$(SEC)=3.0 kDa, Đ(SEC)= 1.09.

Acylation of PEI
General Procedure A.

PyBop (4.84 g, 9.3 mmol) and the corresponding carboxylic acid (Table 1, 9.3 mmol) were dissolved in dry N,N-dimethyl formamide (DMF, 30 mL). DIPEA (2.43 mL, 14.0 mmol) was added dropwise and the mixture was stirred at room temperature. After 2 min, the mixture was transferred into a solution of PEI (200 mg, 4.7 mmol amine groups) in dry DMF (30 mL), followed by stirring at room temperature overnight (14 h) under argon atmosphere. The solvent was evaporated under reduced pressure and the polymer was isolated by dialysis (MWCO=1 kDa) against distilled water followed by freeze-drying. The full conversion of amines was confirmed by $^1$H-NMR spectroscopy and the Kaiser test. In the latter method, the prepared polymers were dissolved in 1 M solution of ninhydrin in ethanol ($c_{pol}$=10 mg mL$^{-1}$) and incubated at 50° C. for 24 h. The absence of coloration indicated full conversion of the amino groups.

TABLE 1

Characteristics of prepared PAOx.

| Polymer | R—COOH[a] | $M_w$ (kDa)[b] | $M_n$ (kDa)[b] | Đ[b] | $T_g$ (° C.)[c] | $\Delta C_p$ (J g$^{-1}$K$^{-1}$)[c] | $T_d$ (° C.)[d] |
|---|---|---|---|---|---|---|---|
| PEtOx | — | 7.6 | 7.1 | 1.07 | 53.2 | 0.51 | 388 |
| PMeOx | Acetic acid | 7.9 | 7.5 | 1.15 | 73.7 | 0.40 | 354 |
| PMeOMeOx | MeOMeCOOH | 9.0 | 8.3 | 1.10 | 32.4 | 0.56 | 356 |
| PEtOMeOx | EtOMeCOOH | 8.4 | 7.1 | 1.18 | 20.2 | 0.59 | 332 |
| PMeOEtOx | MeOEtCOOH | 8.3 | 7.5 | 1.11 | 21.4 | 0.78 | 334 |
| PEtOEtOx | EtOEtCOOH | 9.3 | 8.3 | 1.18 | 8.0 | 0.52 | 320 |
| PDEGOx | MeOEtOEtOMeCOOH | 14.7 | 12.4 | 1.18 | −25.2 | 0.85 | 312 |

[a]Carboxylic acid used for PEI acylation.
[b]Determined by SEC with light scattering detection.
[c]Determined by DSC from the second heating run (5K min$^{-1}$).
[d]Degradation temperature at 5% mass loss determined by TGA.

Poly(2-methyl-2-oxazoline) (PMeOx) was synthesized according to the general procedure A using acetic acid in 78% yield. $^1$H NMR (δ in CD$_3$OD, 400 MHz, ppm): 3.63-3.45 (m, 4H), 2.20-1.94 (s, 3H).

Poly(2-methoxymethyl-2-oxazoline) (PMeOMeOx) was synthesized according to the general procedure A using acetic acid in 86% yield. $^1$H NMR (δ in CD$_3$OD, 400 MHz, ppm): 4.27-4.09 (m, 2H), 3.63-3.46 (m, 4H), 3.41 (s, 3H).

Poly(2-ethoxymethyl-2-oxazoline) (PEtOMeOx) was synthesized according to the general procedure A using acetic acid in 79% yield. $^1$H NMR (δ in CD$_3$OD, 400 MHz, ppm): 4.36-4.18 (m, 2H), 3.70-3.45 (m, 6H), 1.28-1.23 (m, 3H).

Poly(2-methoxyethyl-2-oxazoline) (PMeOEtOx) was synthesized according to the general procedure A using acetic acid in 90% yield. $^1$H NMR (δ in CDCl$_3$, 400 MHz, ppm): 3.73-3.60 (m, 2H), 3.58-3.35 (m, 4H), 3.29 (s, 3H), 2.68-2.40 (m, 2H).

Poly(2-ethoxyethyl-2-oxazoline) (PEtOEtOx) was synthesized according to the general procedure A using acetic acid in 85% yield. $^1$H NMR (δ in CD$_3$OD, 400 MHz, ppm): 3.78-3.43 (m, 8H), 2.74-2.55 (m, 2H), 1.21-1.09 (m, 3H).

Poly(2[methoxy-ethoxy-ethoxymethyl]-2-oxazoline) (PDEGOx) was synthesized according to the general procedure A using acetic acid in 71% yield. $^1$H NMR (δ in CD$_3$OD, 400 MHz, ppm): 4.35-4.25 (m, 2H), 3.74-3.47 (m, 12H), 3.36 (s, 3H).

Synthesis of poly(2-dimethylamino-2-oxazoline) (PDMAOX)

N,N-dimethylcarbamoyl chloride (carbamic acid chloride) (1 g, 9.3 mmol) was dissolved in dry N,N-dimethyl formamide (DMF, 30 mL). DIPEA (2.43 mL, 14.0 mmol) was added and the mixture was transferred into a solution of PEI (200 mg, 4.7 mmol amine groups) in dry DMF (30 mL), followed by stirring at room temperature overnight (14 h) under argon atmosphere. The solvent was evaporated under reduced pressure and the polymer was isolated by dialysis (MWCO=1 kDa) against distilled water followed by freeze-drying. The full conversion of amines was confirmed by $^1$H-NMR spectroscopy and the abovementioned Kaiser test. PDMAOX was obtained in 63% yield. $^1$H NMR (δ in D20, 400 MHz, ppm): 3.68-3.51 (m, 4H), 2.78-2.92 (m, 6H).

Labeling of Polymers with Fluorescein

Azide-functionalized PAOx (80 mg) and DTT (10 equiv of azide) were dissolved in phosphate buffered-saline (PBS, 2 mL, pH=7.4, c=150 mM) and stirred at room temperature overnight (16 h). The resulting amine-functionalized PAOx was recovered by gel filtration on a Sephadex PD-10 column using distilled water as an eluent and isolated by freeze-drying. The obtained solid polymer (72-81 mg) and FITC (2 equiv) were dissolved in DMF (0.5 mL) followed by addition of triethylamine (3 equiv). After stirring at room temperature overnight, the reaction mixture was diluted with distilled water (0.5 mL) and separated by gel filtration on a Sephadex PD-10 column using distilled water as an eluent and isolated by freeze-drying the polymer fractions. This separation procedure was repeated to obtain the pure fluorescein-labeled PAOx samples (64-77 mg) as dark-orange solids.

Characterization of Polymers.

Gas chromatography (GC) was used to monitor the CROP of EtOx employing an Agilent 7890A system equipped with a VWR Carrier-160 hydrogen generator and an Agilent HP-5 column of 30 m length and 0.32 mm diameter. An FID detector was used, and the inlet was set to 240° C. with a split injection ratio 25:1. Hydrogen was used as carrier gas at a flow rate of 2 mL Size exclusion chromatography (SEC) was used to determine the molecular weights ($M_m$—mass-averaged molecular weight, $M_n$—number-averaged molecular weight) and dispersity (Đ=$M_m/M_n$) of the prepared polymers. This was performed using an HPLC Ultimate 3000 system (Dionex, USA) equipped with a SEC column (TSKgel SuperAW3000 150×6 mm, 4 µm for PAOx, respectively TSKgel G5000PWXL-CP 300×7.8 mm, 10 µm for PEI). Three detectors, UV/VIS, refractive index (RI) Optilab®-rEX and multi-angle light scattering (MALS) DAWN EOS (Wyatt Technology Co., USA) were employed; with a methanol and sodium acetate buffer (0.3 M, pH 6.5) mixture (80:20 vol %, flow rate of 0.5 mL min') as mobile phase. A differential refractometer (Wyatt Optilab T-rEX) was used to determine the do/dc values of the polymers (Table 2).

TABLE 2

Refractive index increments (dn/dc) of the synthesized polymers in a 80:20 vol % mixture of methanol and sodium acetate buffer (0.3M, pH = 6.5).

| Polymer | dn/dc |
|---|---|
| PEtOx | 0.178 |
| PEI | 0.169 |
| PMeOx | 0.181 |
| PMeOMeOx | 0.154 |
| PEtOMeOx | 0.161 |
| PMeOEtOx | 0.172 |

TABLE 2-continued

Refractive index increments (dn/dc) of the synthesized polymers in a 80:20 vol % mixture of methanol and sodium acetate buffer (0.3M, pH = 6.5).

| Polymer | dn/dc |
|---|---|
| PEtOEtOx | 0.175 |
| PDEGOx | 0.153 |

The molecular weights of the fluorescein-labeled PAOx were determined by SEC using an Agilent 1260-series HPLC system equipped with a 1260 ISO-pump, a 1260 automatic liquid sampler, a thermostatted column compartment at 50° C. equipped with two PLgel 5 μm mixed-D columns and a precolumn in series, a 1260 diode array detector and a 1260 RI detector. The used eluent was DMA containing 50 mM of LiCl at a flow rate of 0.5 ml min'. Molar mass values and Ð values are calculated against narrow dispersity PMMA standards.

High performance liquid chromatography (HPLC) analyses were performed with a HPLC Ultimate 3000 system (Dionex, USA) using a reverse-phase column (Chromolith Performance RP-18e 100×4.6 mm, Merck, Germany) and multi-angle light scattering (MALS) DAWN EOS detection. A gradient of acetonitrile/water from 5% to 95% in 10 min was used as a mobile phase (flow rate of 2 mL min-1).

Nuclear magnetic resonance (NMR) spectra were measured with a Bruker Advance MSL 400 MHz NMR spectrometer. All chemical shifts are given in ppm.

Fourier transformed infrared (FTIR) spectra were recorded on an IRAffinity-1 Shimadzu FT-IR spectrophotometer with MIRacle Attenuated Total Reflectance Attachment at resolution of 4 cm$^{-1}$ accumulating 50 scans.

The cloud point temperature ($T_{cp}$) of PEtOEtOx was measured on a Crystal 16™ parallel crystallizer turbidimeter (Avantium Technologies) connected to a recirculation chiller at concentration $c_{pol}$=10 mg mL and heating rate of 0.5° C. min$^{-1}$. The $T_{cp}$ was reported as the temperature with 50% transmittance in the heating run. Additionally, the $T_{cp}$ was measured by dynamic light scattering (DLS) using a Zetasizer NanoZS instrument, Model ZEN3600 (Malvern Instruments, UK). The polymer was dissolved in distilled water ($c_{pol}$=10 mg mL$^{-1}$) and filtered through an 0.22 μm PVDF syringe filter. The total light scattering intensity was determined at a scattering angle of θ=173° and the DTS (Nano) program was used to evaluate the data. After each increase in temperature (0.5° C. step), the sample was equilibrated for 5 min followed by the DLS measurement. The $T_{CP}$ corresponds to the onset of the increase of the scattered light intensity.

Differential scanning calorimetry (DSC) was performed on a Mettler-Toledo DSC1 module in a nitrogen atmosphere with a heating/cooling rate of 5° C. min$^{-1}$. Indium was used as a standard for temperature and enthalpy calibrations. The values of the glass transition temperature ($T_g$) were determined from the second heating run.

Thermogravimetric analyses (TGA) were performed on a Mettler-Toledo TGA/SDTA851e in a nitrogen atmosphere in the range from 25° C. to 800° C. with a heating rate of 10° C. min$^{-1}$. The samples were dried in a vacuum oven at 40° C. for 24 h prior to use.

The fluorescein content in PAOx-fluorescein conjugates was measured by UV/VIS spectrometry (Evolution 220 Spectrometer, Thermo Scientific) in sodium carbonate buffer (pH=9.2, c=0.15 M) at 25° C. (ε=11 500 l mol$^{-1}$ cm$^{-1}$; λ=488 nm). All measurements were performed in triplicate.

Partition coefficient of PAOx-fluorescein conjugates was determined by extraction experiment according to a literature procedure (Callahan et al., 2006). Briefly, PAOx-fluorescein conjugates (2 mg) were dissolved in PBS (pH=7.4, 150 mM) to achieve equimolar solutions with comparable absorbance at 488 nm ($A_0 \approx 1$). From this stock solutions, 2 mL were aliquoted into the clean vial followed by addition of either 1-octanol or dichloromethane (2 mL). The sealed vial was mixed by shaking for at least 2 h followed by standing for another 2 h to allow the phase separation. The concentration in each fraction was determined by fluorescent spectrophotometry ($\lambda_{ex}$=480 nm, $\lambda_{em}$=518 nm). For this, standard curves of each polymer were created using both 1-octanol/dichloromethane saturated with PBS or PBS saturated with 1-octanol/dichloromethane, respectively. The partition coefficient (P) was calculated as $P=c_{org}/c_{PBS}$; where $c_{org}$ is polymer concentration in the organic phase (1-octanol or dichloromethane) and $c_{PBS}$ being the polymer concentration in PBS. All measurements were performed in triplicate.

The in vitro cytotoxicity of the prepared PAOx was evaluated using the cervical carcinoma cell line HeLa. $5 \times 10^4$ of HeLa cells were seeded in 100 μL of media into 96-well flat-bottom TPP plates (Thermo-Fisher Scientific, Czech Republic) for 24 h before adding the polymers, of which the concentration was varied in the range 100-0.1 μg ml$^{-1}$. The cells were cultivated at 37° C. for 72 h under 5% CO2 atmosphere. AlamarBlue® cell viability reagent (10 μl; Thermo-Fischer Scientific) was added to each well and incubated at 37° C. for 4 h. The active component of the AlamarBlue reagent resazurin was reduced to the highly fluorescent resorufin only in viable cells. Its fluorescence was detected in a Synergy Neo plate reader (Bio-Tek; Winooski, VT, USA) using excitation at 570 nm and emission at 600 nm. As a control, the cells cultivated in medium without PAOx were utilized. The assay was repeated two to three times in triplicate and quadruplicate.

Results and Discussion

The synthetic approaches used in this work are depicted in Scheme 1.

Scheme 1. Synthesis of new PAOx via acylation of well-defined PEI

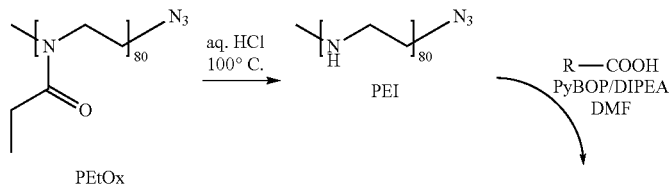

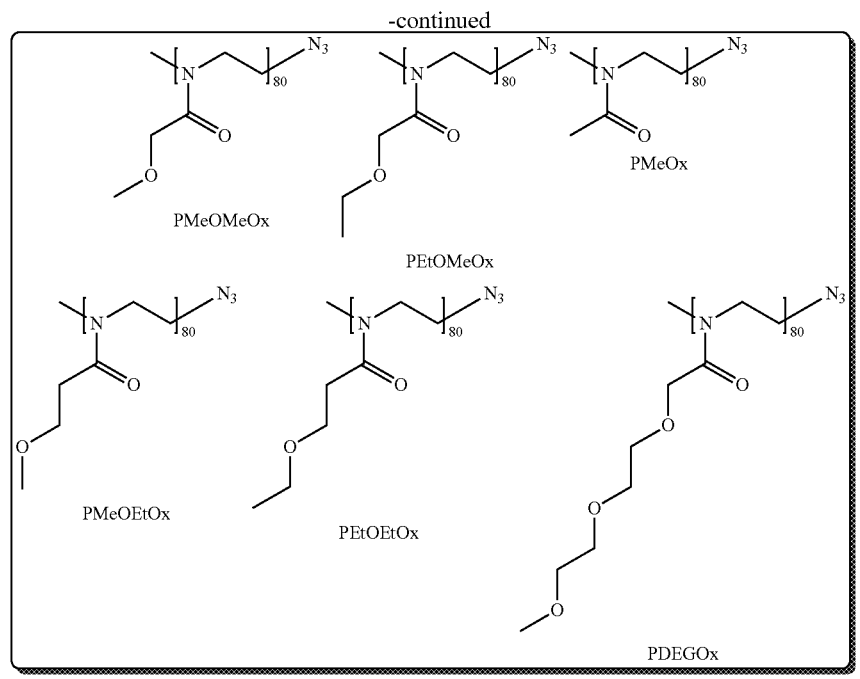

Figure 2:
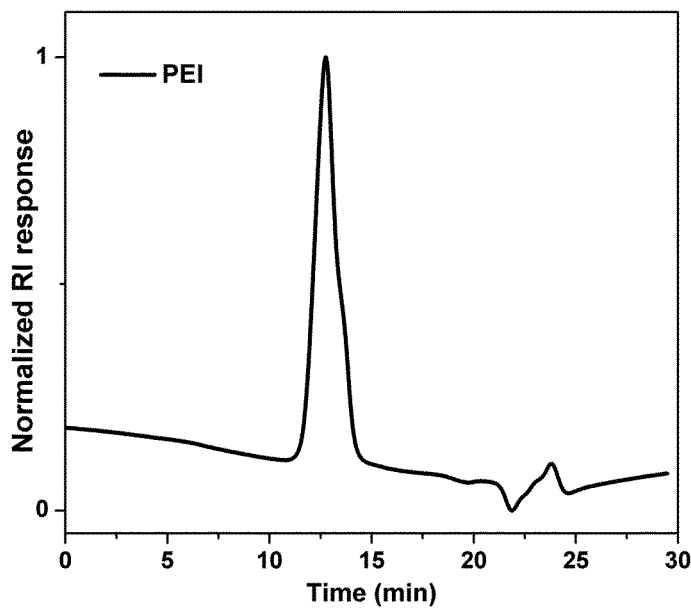
FIG. 2. SEC trace of the synthesized polyethyleneimine (PEI).

The starting material, a well-defined poly(2-ethyl-2-oxazoline) (PEtOx) having degree of polymerization DP=80, was synthesized by living cationic ring-opening polymerization (CROP) of EtOx in acetonitrile followed by the termination of the polymerization with sodium azide. The latter step introduces the chain-end azide group suitable for further functionalization. The obtained PEtOx was subjected to a controlled acidic hydrolysis in aqueous hydrochloric acid to yield linear PEI with a low molar mass distribution (Đ=1.09, FIG. 2).

Figure 3:
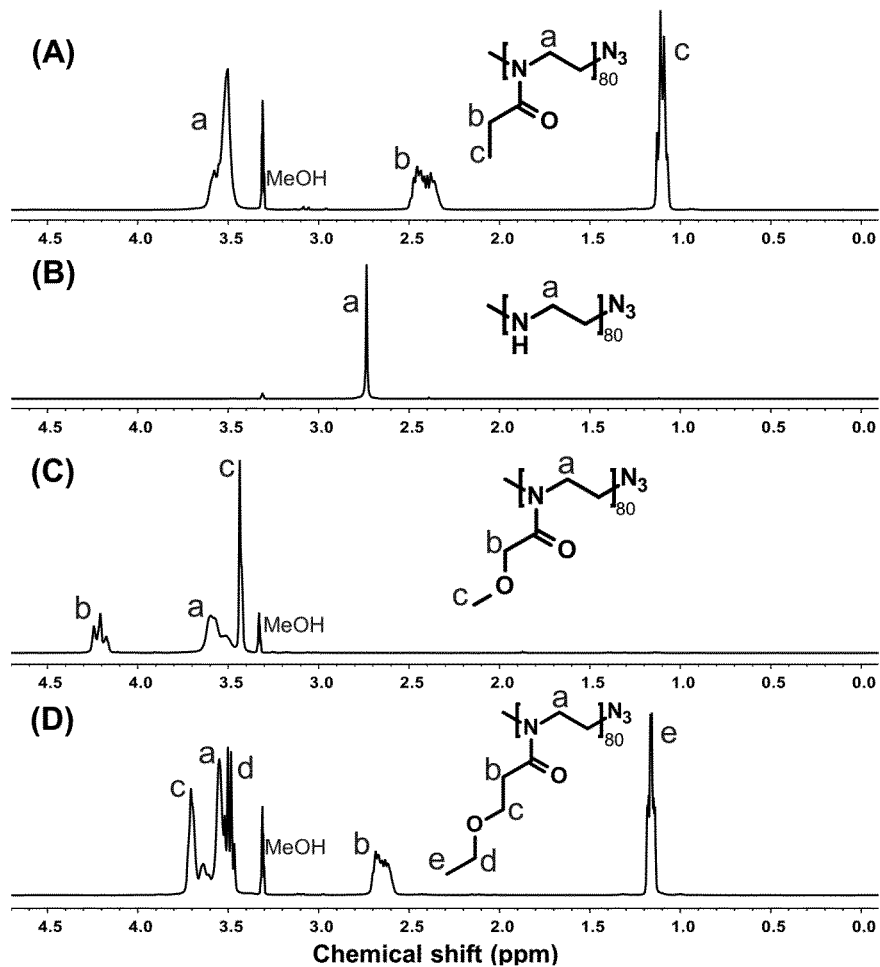
FIG. 3. Representative $^1$H NMR spectra (400 MHz) of PEtOx (A), PEI (B), PMeOMeOx (C) and PEtOEtOx (D) in CD$_3$OD.
Figure 4:
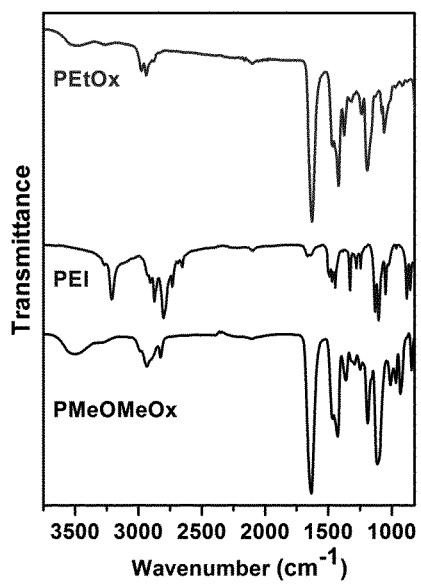
FIG. 4. Representative FTIR spectra of synthesized PEtOx, PEI and PMeOMeOx.

The full conversion was confirmed by $^1$H NMR spectroscopy, where both signals of the PEtOx side-chains completely disappeared and the main backbone ethylene signal was shifted from δ 3.5 ppm (PEtOx ethylene groups adjacent to the amide) to δ 2.8 ppm (PEI ethylene adjacent to amine) (FIG. 3). The FTIR spectroscopy also revealed the disappearance of characteristic PEtOx amide carbonyl vibration at 1620 cm$^{-1}$ (FIG. 4) while a new strong peak appeared at 3214 cm$^{-1}$, which can be assigned to the N—H stretch vibration of PEI. Finally, the presence of the chain-end azide group was confirmed by its characteristic vibration at 2100 cm$^{-1}$.

For certain biomedical applications, such as non-fouling coatings and drug carriers, the high hydrophilicity and biocompatibility of new polymers is desired. Therefore, the obtained PEI was re-acylated with a series of relatively hydrophilic ether-containing carboxylic acids (Table 1) to obtain a library of new water-soluble PAOx. Additionally, acetic acid was used for the synthesis of the widely used hydrophilic PMeOx to prove that its properties do not differ from those of the same polymer prepared by CROP. Inspiration for the synthesis of such PAOx via acylation rather than the synthesis and polymerization of novel monomer was our previous unsuccessful attempt to synthesize PMeO-EtOx. During the monomer synthesis, the base-catalyzed elimination of methanol occurred, resulting in MeOEtOx heavily contaminated with 2-vinyl-2-oxazoline (FIG. 1). The new acylation protocol overcomes this difficulty.

The PEI amidation was performed by a standard peptide coupling protocol using (benzotriazol-1-yloxy)tripyrrolidinophosphonium hexafluorophosphate (PyBOP) as a coupling agent, DIPEA as base and dry DMF as solvent yielding the new PAOx as colorless products. Note that this method was preferred over the use of acid chlorides as the latter leads to brown coloration of the polymers, presumably due to partial oxidation of the amino groups. To ensure full conversion of the secondary amines, the reaction mixture was stirred overnight. This approach is rather universal and can be used for a variety of carboxylic acids to quickly synthesize libraries of different PAOx without the need of monomer synthesis and purification, which can be difficult or time-consuming. Additionally, it can be used for the synthesis of random PAOx copolymers in cases, where different monomer reactivities cause gradient copolymer structures (e.g., MeOx with PhOx). As this standard protocol can be used for coupling of amino acids with unprotected hydroxyl groups (e.g., serine), we attempted to acylate PEI with lactic acid with the aim to make a very hydrophilic poly(2-hydroxy-2-ethyl-2-oxazoline).

Figure 5:
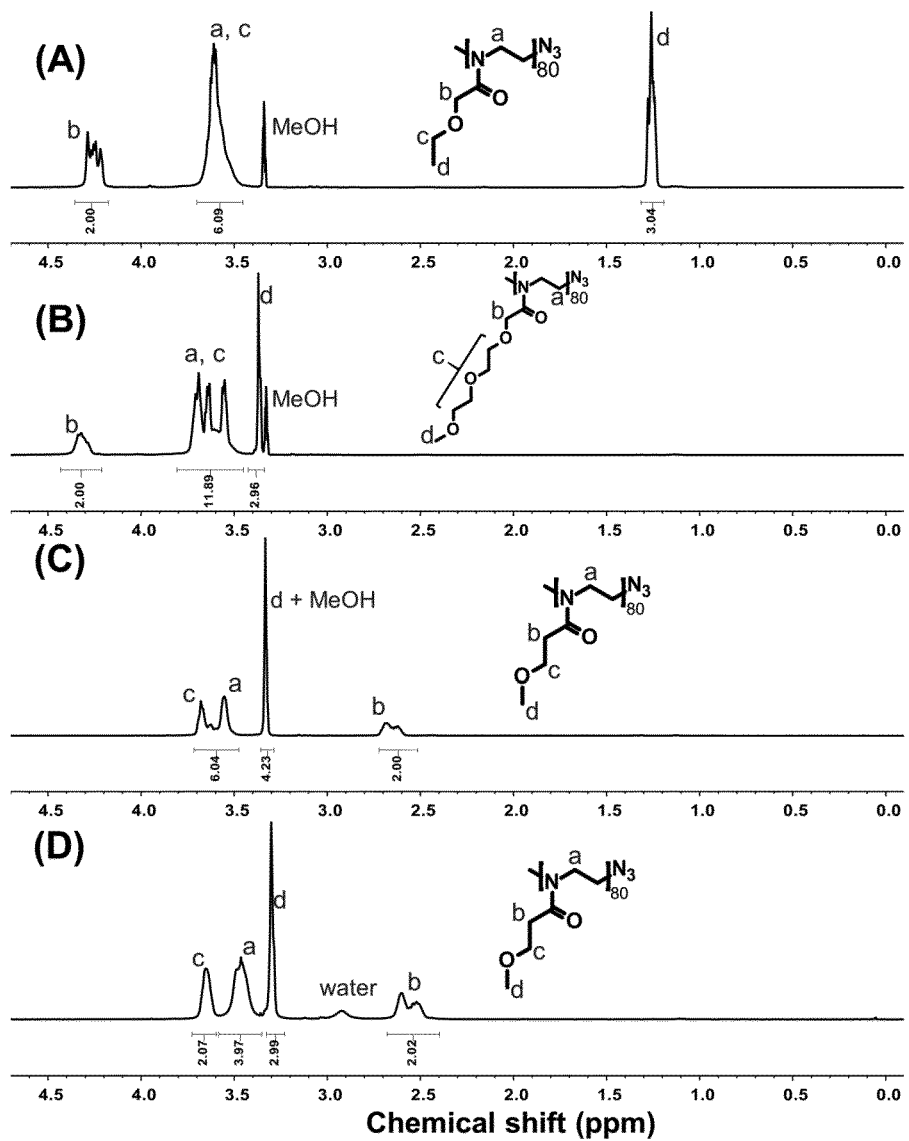
FIG. 5. $^1$H NMR spectra of PEtOMeOx (A), PDEGOx (B) and PMeOEtOx (C) in CD$_3$OD and PMeOEtOx (D) in CDCl$_3$.
Figure 6:
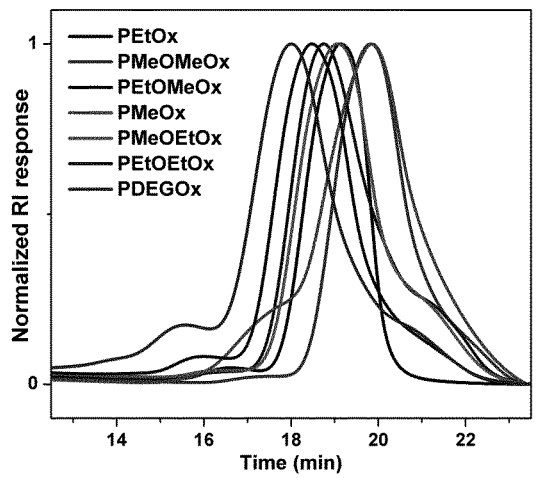
FIG. 6. SEC traces of prepared PAOx polymers.

The obtained hydrophilic PAOx were analyzed by various methods including NMR, FTIR spectroscopy, SEC, HPLC, turbidimetry, DLS and DSC. The $^1$H NMR spectroscopy showed the complete disappearance of PEI signal at δ 2.8 ppm, while new peaks originating from the PAOx backbone (δ 3.4-3.6 ppm) and side chains appeared (FIG. 1 and FIG. 5). In the case of the potential signal overlap (e.g., PEtO-EtOx), the polymer structure was confirmed by $^1$H-$^1$H COSY NMR spectra (data not shown). Additionally, the quantitative conversion of amines was confirmed by a Kaiser test, for which synthesized polymers were dissolved in ninhydrin solution. While the color of the PEI sample turned dark-brown after several minutes at room temperature, the color of the obtained PAOx polymers remained unchanged even after one day of heating at 50° C. (data not shown). The FTIR spectroscopy revealed the disappearance of the PEI N—H vibration at 3214 cm$^{-1}$, while a strong band corresponding to the amide carbonyl vibration appeared at ~1630 cm$^{-1}$ and the characteristic "umbrella" vibration of methyl group was observed around 1370 cm$^{-1}$. Furthermore, the polymers containing ether groups showed strong C—O stretching vibrations at ~1100 cm$^{-1}$. As many biological properties of the polymers depend on their size (e.g., renal clearance, biodistribution, cellular uptake), a high uniformity of the polymer size is desired. In this work, all synthesized polymers were well defined, with low molar mas distribution (Đ<1.2), despite some minor shouldering in the SEC chromatogram due to some unavoidable (at least under the used polymerization conditions) chain transfer and chain coupling side reactions and/or column interactions (FIG. 6; Table 1).

The thermal properties of the new PAOx were studied by differential scanning calorimetry (DSC). All polymers exhibit amorphous behavior with glass transition temperatures ($T_g$) in the range of −25-74° C. (Table 1). The low $T_g$ of amorphous polymers can be beneficial in many respects as their high chain flexibility generally leads to faster dissolution. Also, the higher chain segment mobility is beneficial in the construction of various self-assembling architectures, increasing the rate of chain association/dissociation and facilitating the reproducible formation of equilibrium structures, or in the construction of magnetic resonance imaging (MRI) contrast agents, where the high chain mobility ensures fast transverse relaxation and high MRI contrast. Finally, the low-$T_g$ polymers can be used as plasticizers to improve mechanical properties of various polymer blends. To date, the lowest $T_g$ achieved within the PAOx family was reported to be −6° C. for poly(2-(3-ethylheptyl)-2-oxazoline). In the current study, the PDEGOx sample showed an even lower $T_g$ of −25° C. This low $T_g$ of PDEGOx can be explained by its structural similarity with low molar mass polyethylene glycol (PEG) that exhibits low $T_g$ due to the low rotational activation energy of its chain segments. The second polymer with a $T_g$ significantly lower than room temperature is PEtOEtOx ($T_g$=8° C.). The other ether-containing PAOx (PMeOMeOx, PMeOEtOx and PEtOMeOx) display $T_g$ values around room temperature (20-32° C.; Table 1)

The thermal stability of the new PAOx was determined by thermogravimetric analysis (TGA). All the polymers were stable up to a temperature of at least 300° C. (Table 1). With further heating, the polymers started degrading. The non-ether containing polymers (PEtOx and PMeOx), as well as the polymers containing a methylene group between the amide carbonyl and the ether (PMeOMeOx, PEtOMeOx and PDEGOx) degraded in one step. On the other side, the polymers containing ethylene group between the amide carbonyl and ether (PMeOEtOx and PEtOEtOx) degraded in two steps. The first degradation step (at ~320-335° C.) can be explained by thermal elimination of the alkoxy substituent to obtain 2-vinyl-2-oxazoline units, while the second step (at ~400° C.) indicates the full degradation of polymers.

Figure 7:
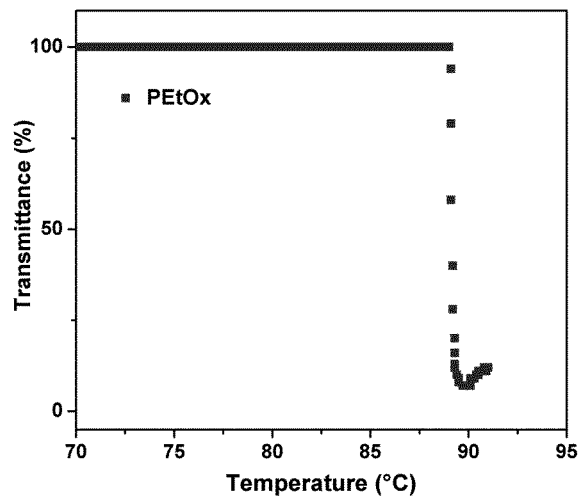
FIG. 7. LCST behavior of synthesized PEtOx: Temperature-induced transmittance change ($c_{pol}$=10 mg mL$^{-1}$).
Figure 8:
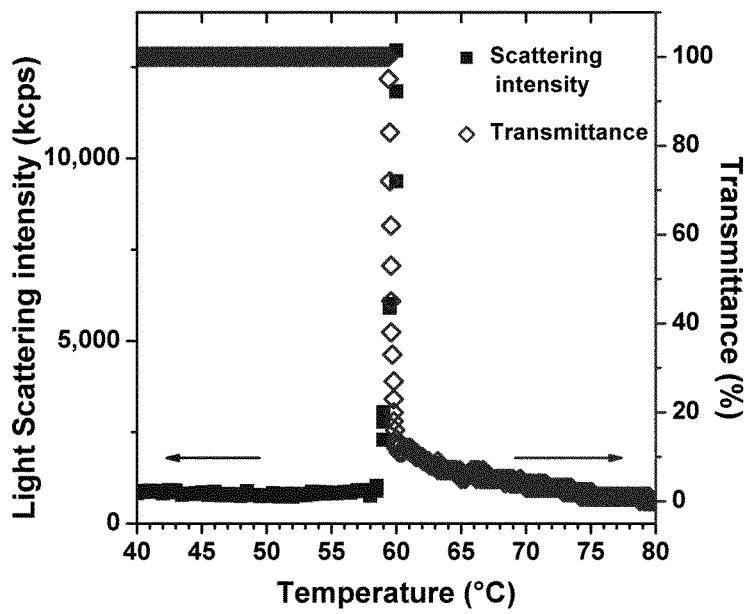
FIG. 8. LCST behavior of PEtOEtOx in water ($c_{pol}$=10 mg mL$^{-1}$) as determined by DLS (blue squares) and turbidimetry (red diamonds).

All the synthesized polymers were water-soluble at room temperature with a solubility higher than 100 mg mL$^{-1}$ (maximum concentration that was tested). As some PAOx (e.g., PEtOx, PPrOx) were reported to exhibit lower critical solution temperature (LCST) behavior in water, the aqueous solubility of the newly synthesized polymers at different temperatures was studied by turbidimetry. Besides PEtOx, which shows a cloud point temperature ($T_{CP}$) of 89° C. (FIG. 7), the only polymer exhibiting LCST behavior in water within the measured range (10-95° C.) was PEtOEtOx with a $T_{CP}$ of 59.5° C. (FIG. 8). To gain more detailed insight into its phase separation, the self-assembly of PEtOEtOx was further investigated by dynamic light scattering (DLS) revealing a very similar value of $T_{CP}$ of 59° C. The LCST behavior of PEtOEtOx may be interesting for advanced thermoresponsive self-assembling architectures.

The hydrophilicity of a polymer plays a key role in its potential in biomedical applications. Extremely hydrophilic polymers possess a strong hydration layer, which protects them from the unwanted interactions with blood proteins in vivo. This so called "stealth behavior" results in improved polymer pharmacokinetics as they evade plasma opsonization and clearance by mononuclear phagocytic system. Therefore, the synthesis of extremely hydrophilic polymers is desired.

Figure 9:
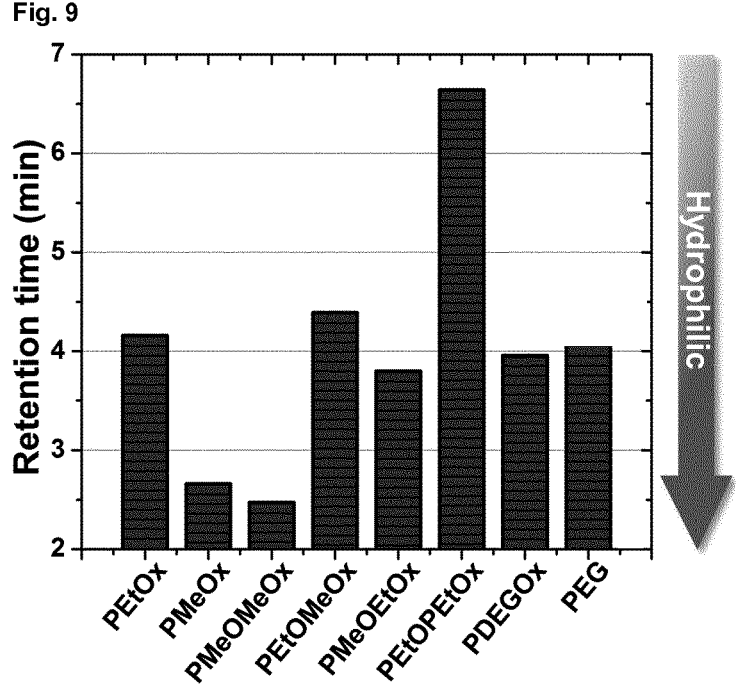
FIG. 9. Reversed phase HPLC retention times of prepared PAOx and PEG.
Figure 10:
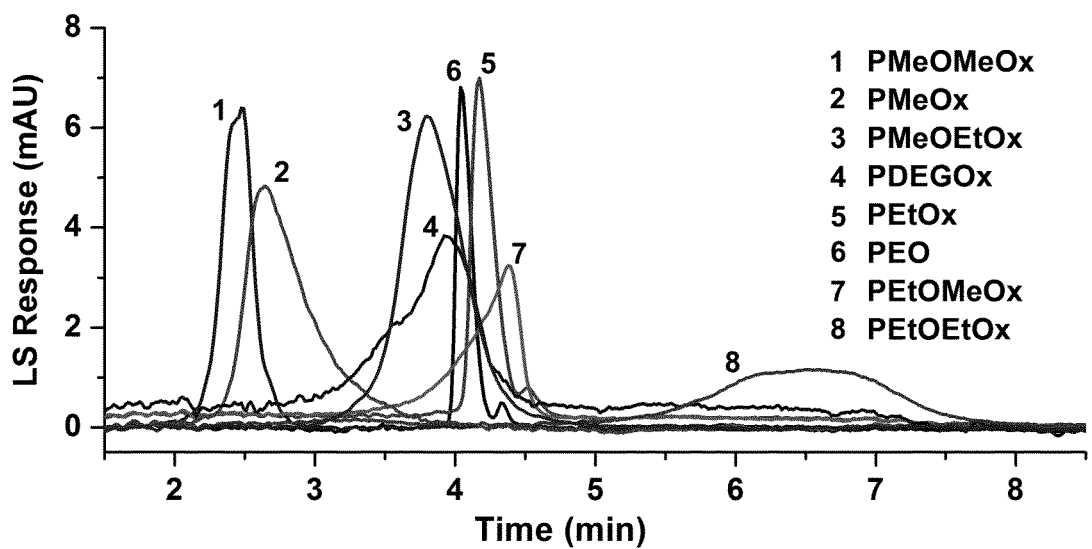
FIG. 10. HPLC chromatograms of the synthesized polymers and PEO using a solvent gradient from 5 to 95% water in acetonitrile in 10 min, flow rate of 2 mL min$^{-1}$.

Herein, we assessed the relative hydrophilicity of the prepared polymers by high performance liquid chromatography (HPLC) on a reversed phase column (C18). Multi-angle light scattering detection was used as the polymers have very low UV absorption. The higher hydrophilicity of polymers is indicated by a lower retention time in HPLC due to the lower interactions with the hydrophobic column stationary phase. Within the prepared PAOx series, the ether-containing polymer with the shortest side chain (PMeOMeOx) showed the highest hydrophilicity (FIGS. 9 and 10), even slightly higher than PMeOx, which was considered as the most hydrophilic PAOx so far. As such, our first-time synthesis of "superhydrophilic" PMeOMeOx might provide a significant progress in the field of new "stealth" biopolymers, which we will explore in future work. On the other side, the most hydrophobic polymer from the series, PEtOEtOx, shows significant interactions with the column surface. This more amphiphilic character of PEtOEtOx is also reflected in its abovementioned LCST behavior. Besides PMeOMeOx, PMeOx and PEtOEtOx, all prepared polymers possess a hydrophilicity that is comparable to PEG standard. Interestingly, we found a significant difference in hydrophilicity between the isostructural PMeOEtOx and PEtOMeOx, differing only in the position of the side-chain ether group. The higher hydrophobicity of PEtOxMeOx can be attributed to the closer distance of the solvated ether group to the polymer backbone, leaving more hydrophobic ethyl groups exposed for interactions with the hydrophobic column surface. This observation is in line with the previous report on lower hydrophilicity of poly(2-ethyl-2-oxazoline) compared to the isomeric poly(2-methyl-2-oxazine)s that has an additional methylene group in the main chain rather than the side chain (Bloksma et al., 2012).

To further investigate the hydrophilicity of the synthesized PAOx, they were conjugated with the fluorescein dye. First, the chain-end azide group was reduced with DL-dithiothreitol (DTT) in PBS. The obtained polymer chain-end amines were then functionalized with fluorescein by coupling with fluorescein isothiocyanate (FITC). The polymer-fluorescein conjugates (F-PAOx) had relatively high chain-end functionality (>60%) and acceptable molar mass distribution (Table 3).

TABLE 3

Characteristics of the prepared polymer-fluorescein conjugates.

| Polymer | $M_n$ (kDa)$^a$ | Đ$^a$ | $f_{FITC}{}^b$ |
|---|---|---|---|
| F-PEtOx | 18.9 | 1.11 | 0.60 |
| F-PMeOx | 19.3 | 1.19 | 0.64 |
| F-PMeOMeOx | 18.5 | 1.19 | 0.88 |
| F-PEtOMeOx | 16.0 | 1.25 | 0.61 |
| F-PMeOEtOx | 16.8 | 1.20 | 0.63 |

TABLE 3-continued

Characteristics of the prepared polymer-fluorescein conjugates.

| Polymer | $M_n$ (kDa)[a] | Đ[a] | $f_{FITC}$[b] |
|---|---|---|---|
| F-PEtOEtOx | 17.8 | 1.21 | 0.87 |
| F-PDEGOx | 24.2 | 1.29 | 0.89 |

[a]Determined by SEC with using PMMA calibration.
[b]Chain end-group functionality determined by UV/VIS spectroscopy.

Figure 11:
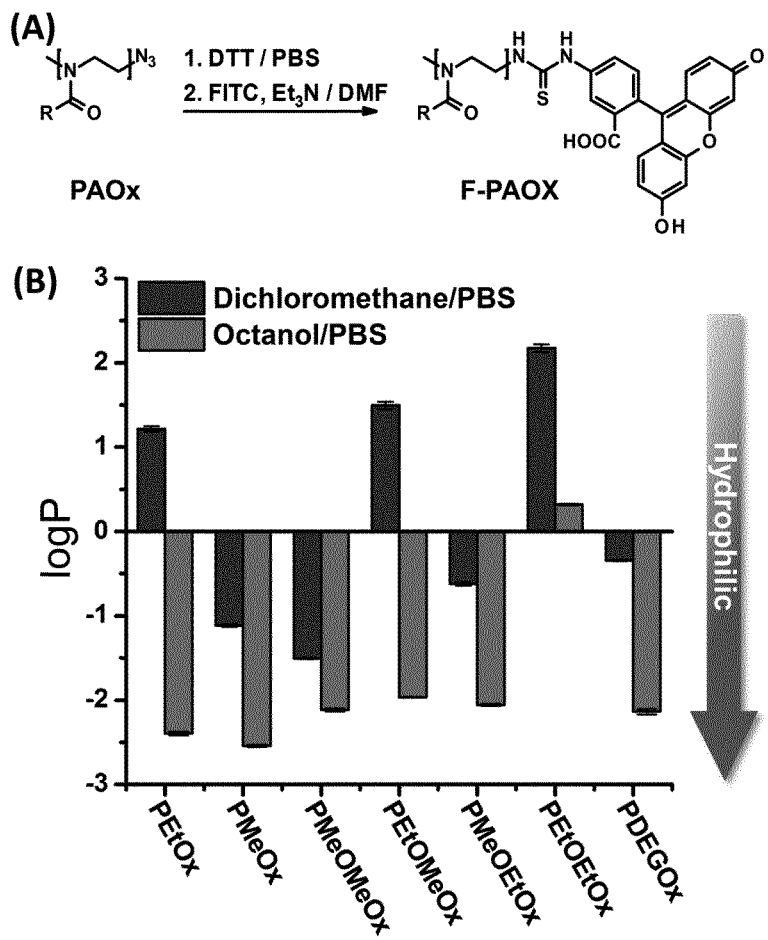
FIG. 11. Labeling of PAOx with fluorescein (A) and partition coefficients of prepared conjugates (B).

Further, the fluorescently labeled polymers were used to quantitatively evaluate their hydrophilicity by measuring their distribution coefficients (P) between PBS and organic solvents (FIG. 11). As the fluorescence intensity of fluorescein label highly depends of pH, the polymer conjugates were dissolved in PBS (pH=7.4) and extracted with 1-octanol, respectively dichloromethane. Surprisingly, the distribution experiments between 1-octanol and PBS suggested higher hydrophilicity of both alkyl side-chain PAOx (PMeOx and PEtOx) compared to the ether side-chain PAOx (including PMeOMeOx). This observation can be explained by the increased hydrogen bonding between the polymer ether groups and 1-octanol, resulting in increased solubility of ether side-chain PAOx in this organic phase. Therefore, 1-octanol was replaced by the non-interacting organic solvent dichloromethane to obtain unbiased measures of polymer hydrophilicity. With this method, the obtained hydrophilicities followed the similar pattern as observed in HPLC experiment, confirming that PMeOMeOx is the most hydrophilic PAOx to date, PEtOEtOx the most hydrophobic polymer from the series and PMeOEtOx being more hydrophilic that the isostructural PEtOMeOx.

Figure 12:
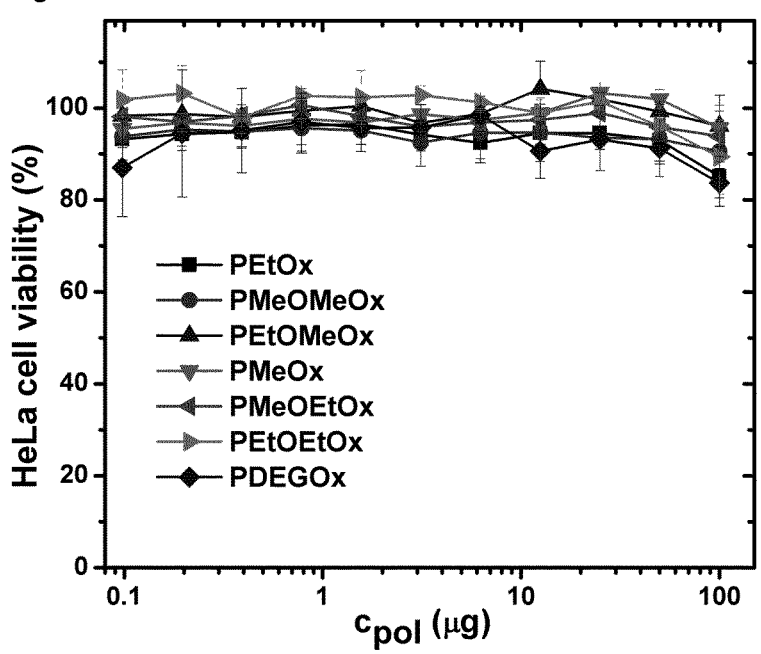
FIG. 12. Cytotoxicity of prepared PAOx: Dependence of HeLa cell viability on PAOx concentration (after 72 h incubation at 37° C.).

The non-cytotoxic character of the synthesized PAOx was confirmed in vitro using an AlamarBlue® cell viability assay in cervical carcinoma HeLa cells. The polymers were incubated with cells for 76 h at 37° C., after which the cell viability was assessed (FIG. 12). All polymers (including PMeOMeOx) were non-cytotoxic in the concentration range of up to 0.1 mg mL$^{-1}$ proving their excellent in vitro biocompatibility. In the future, detailed biological evaluation of the synthesized polymers (especially PMeOMeOx) will be performed, as they possess interesting potential for the construction of new drug/gene delivery systems and surface biocompatibilization.

CONCLUSIONS

In summary, we developed a new method for the synthesis of functional PAOx. The easily available PEtOx is hydrolyzed to a well-defined linear PEI, which is further re-acylated with different carboxylic acids to obtain a series of new PAOx polymers. The described synthetic protocol is universal and can be used for the synthesis of PAOx libraries without the need of preparing particular 2-alkyl-2-oxazoline monomers, as well as avoiding the individual cationic ring opening polymerization procedures.

To demonstrate the versatility of the protocol, we synthesized a series of new highly hydrophilic PAOx and evaluated their physical, chemical and biological properties by different techniques with emphasis on their potential in biomedical research. The relative hydrophilicity of the polymers was assessed, revealing PMeOMeOx as the most hydrophilic PAOx to date, being more hydrophilic than both poly(2-methyl-2-oxazoline) and poly(ethylene glycol), hence being a superhydrophilic polymer. Additionally, PDEGOx shows the lowest reported glass-point temperature within the PAOx family to date. The biomedical potential of synthesized polymers was fortified by an in vitro cell viability assay, where all polymers appeared to be non-cytotoxic at least up to 0.1 mg/mL. Another extremely hydrophilic polymer, poly(2-dimethylamino-2-oxazoline) (PDMAOX) was synthesized by acylation of PEI by N,N-dimethylcarbamoyl chloride. The development of extremely hydrophilic PAOx might lead to an interesting progress in the field of new "stealth" biopolymers. Therefore, an in-depth study of its biological properties will be performed in the near future.

REFERENCES

Bloksma, M. M.; Paulus, R. M.; van Kuringen, H. P.; van der Woerdt, F.; Lambermont-Thijs, H. M.; Schubert, U. S.; Hoogenboom, R., Thermoresponsive Poly (2-oxazine) s. *Macromol. Rapid Commun.* 2012, 33 (1), 92-96.

Callahan, J.; Kopeček, J., Semitelechelic HPMA copolymers functionalized with triphenylphosphonium as drug carriers for membrane transduction and mitochondrial localization. *Biomacromolecules* 2006, 7 (8), 2347-2356.

Das, A.; Theato, P., Activated Ester Containing Polymers: Opportunities and Challenges for the Design of Functional Macromolecules. *Chem. Rev.* 2016, 116(3), 1434-1495.

Kagiya, T.; Narisawa, S.; Maeda, T.; Fukui, K., Ring-opening polymerization of 2-substituted 2-oxazolines. *Journal of Polymer Science Part B: Polymer Letters* 1966, 4 (7), 441-445.

Mees, M. A.; Hoogenboom, R., Functional poly (2-oxazoline) s by direct amidation of methyl ester side chains. *Macromolecules* 2015, 48 (11), 3531-3538.

Mees, M. A.; Effenberg, C.; Appelhans, D.; Hoogenboom, R., Sweet polymers: poly (2-ethyl-2-oxazoline) glycopolymers by reductive amination. *Biomacromolecules* 2016, 17 (12), 4027-4036.

Mees, M. A.; Hoogenboom, R., Full and partial hydrolysis of poly(2-oxazoline)s and the subsequent post-polymerization modification of the resulting polyethylenimine (co)polymers. *Polymer Chemistry* 2018, 9, 4968-4978.

Verbraeken, B.; Monnery, B. D.; Lava, K.; Hoogenboom, R., The chemistry of poly (2-oxazoline)s. *Eur. Polym. J.* 2017, 88, 451-469.

The invention claimed is:

1. A polyoxazoline selected from the group consisting of poly(2-methoxymethyl-2-oxazoline), poly(2-dimethylamino-2-oxazoline), and copolymers having at least one monomeric unit of poly(2-methoxymethyl-2-oxazoline) or poly(2-dimethylamino-2-oxazoline).

2. A composition, comprising:
   at least one polyoxazoline according to claim 1; and
   at least one active ingredient.

3. The composition of claim 2, wherein the at least one active ingredient is a pharmaceutically active ingredient.

4. The composition of claim 2, wherein the at least one active ingredient is a hydrophilic active pharmaceutical ingredient.

5. The composition of claim 2, wherein the composition is a veterinary medicine or a medicine for humans.

6. A substrate having attached thereto, or associated therewith, at least one polyoxazoline according to claim 1.

7. The substrate of claim 6, wherein the substrate is a polymeric support, a metal support, a metal oxide support, a glass support, a quartz support, or a silicon support.

8. The substrate of claim 6, wherein the substrate is a (bio)medical implant, a drug delivery carrier, a biosensor, or a marine coating.

9. The substrate of claim 6, wherein the at least one polyoxazoline is an anti-biofouling coating, a blood half-life extending coating, or a lubricating coating.

10. The substrate of claim 6, wherein the at least one polyoxazoline is a surface modification of the substrate.

11. The polyoxazoline of claim 1, wherein the polyoxazoline is a homopolymer poly(2-methoxymethyl-2-oxazoline).

\* \* \* \* \*

UNITED STATES PATENT AND TRADEMARK OFFICE
CERTIFICATE OF CORRECTION

PATENT NO. : 12,037,456 B2
APPLICATION NO. : 17/293669
DATED : July 16, 2024
INVENTOR(S) : Richard Hoogenboom and Ondrej Sedlacek It is certified that error appears in the above-identified patent and that said Letters Patent is hereby corrected as shown below:

On the Title Page

Column 2, item (56), other publications, cite no 1, delete "eference" and insert --reference--, therefor.

In page 2, Column 1, item (56), other publications, cite no 3, delete "Marcomolecular" and insert --Macromolecular--, therefor.

In the Specification

In Column 6, Line(s) 4 & 5, delete "anti-arrhytmic" and insert --anti-arrhythmic--, therefor.

In Column 6, Line(s) 10, delete "antihyperstensive" and insert --antihypertensive--, therefor.

In Column 6, Line(s) 14, delete "antiprotozola" and insert --antiprotozoal--, therefor.

In Column 6, Line(s) 24, delete "homonolytics" and insert --hemolytics--, therefor.

In Column 6, Line(s) 27, delete "relexants" and insert --relaxants--, therefor.

In Column 6, Line(s) 28, delete "nicotene" and insert --nicotine--, therefor.

In Column 6, Line(s) 29, delete "sedatices" and insert --sedatives--, therefor.

In Column 6, Line(s) 46, delete "biofiim" and insert --biofilm--, therefor.

In Column 6, Line(s) 65, delete "terephtalate" and insert --terephthalate--, therefor.

In Column 12, Line(s) 39, after "2 mL", insert --min$^{-1}$.--.

In Column 12, Line(s) 51, after "0.5 mL", delete "min'" and insert --min$^{-1}$--, therefor.

Signed and Sealed this
Fourth Day of March, 2025

Coke Morgan Stewart
*Acting Director of the United States Patent and Trademark Office*

In Column 12, Line(s) 53, delete "do/dc" and insert --dn/dc--, therefor.

In Column 13, Line(s) 19, after "0.5 ml", delete "min'." and insert --min$^{-1}$.--, therefor.

In Column 13, Line(s) 30, after "2 mL", delete "min-1" and insert --min$^{-1}$--, therefor.